(12) United States Patent
Dausch et al.

(10) Patent No.: US 7,556,637 B2
(45) Date of Patent: Jul. 7, 2009

(54) FORCEPS-LIKE SURGICAL ELEMENT

(75) Inventors: Hermann Dausch, Tuttlingen (DE); Andreas Dausch, Tuttlingen (DE)

(73) Assignee: Hermann Dausch Medizintechnik GmbH (DE)

( * ) Notice: Subject to any disclaimer, the term of this patent is extended or adjusted under 35 U.S.C. 154(b) by 720 days.

(21) Appl. No.: 10/484,412

(22) PCT Filed: Jul. 3, 2002

(86) PCT No.: PCT/EP02/07315

§ 371 (c)(1), (2), (4) Date: Jan. 20, 2004

(87) PCT Pub. No.: WO03/009765

PCT Pub. Date: Feb. 6, 2003

(65) Prior Publication Data

US 2004/0249410 A1  Dec. 9, 2004

(30) Foreign Application Priority Data

Jul. 21, 2001 (DE) .................. 201 12 141 U
Jul. 25, 2001 (DE) .................. 201 12 281 U
Mar. 1, 2002 (DE) .................. 202 03 239 U

(51) Int. Cl.
*A61B 17/28* (2006.01)
(52) U.S. Cl. ..................... 606/208; 606/210
(58) Field of Classification Search ......... 606/205–210, 606/139, 144, 1, 142, 170, 174, 180; 600/434, 600/585
See application file for complete search history.

(56) References Cited

U.S. PATENT DOCUMENTS

| 4,433,687 A |   | 2/1984  | Burke |
|---|---|---|---|
| 5,281,235 A | * | 1/1994  | Haber et al. ............... 606/208 |
| 5,368,596 A |   | 11/1994 | Burkhart |
| 5,498,256 A | * | 3/1996  | Furnish .................... 606/208 |
| 5,501,698 A |   | 3/1996  | Roth |

(Continued)

FOREIGN PATENT DOCUMENTS

DE   1 836 439 U   8/1961

(Continued)

OTHER PUBLICATIONS

International Search Report for PCT/EP02/07315 Dated Nov. 19, 2002.

(Continued)

*Primary Examiner*—Kevin T Truong
(74) *Attorney, Agent, or Firm*—Bachman & LaPointe, P.C.

(57) ABSTRACT

The invention relates to a forcep-like surgical element comprising lip profiles, which are provided at one end, can be guided in relation to one another, and which delimit a clamping mouth or form a pair of scissors. According to the invention, two handle elements, which can be moved in relation to one another, are provided as an actuating unit. Each handle element is joined to at least one of the lip profiles via a cord element. The handle elements or handle parts are scissor handles, which can pivot relative to one another and each have a holding eye or similar implements that define an angle with the surface of their cord element, said surface delimiting the clamping mouth. This angle is formed in a variable manner on each of the scissor handles for moving the lip profiles.

11 Claims, 8 Drawing Sheets

U.S. PATENT DOCUMENTS 5,906,629 A 5/1999 Oren et al.
5,928,263 A * 7/1999 Hoogeboom ................ 606/205

FOREIGN PATENT DOCUMENTS

| DE | 33 43 867 A | 6/1985 |
| DE | 42 38 619 A1 | 5/1994 |
| DE | 296 16 210 U1 | 9/1996 |
| DE | 197 13 067 A | 10/1998 |

OTHER PUBLICATIONS

German Office Action for German Patent No. 102 93 222.0-35 dated Dec. 20, 2007.

* cited by examiner

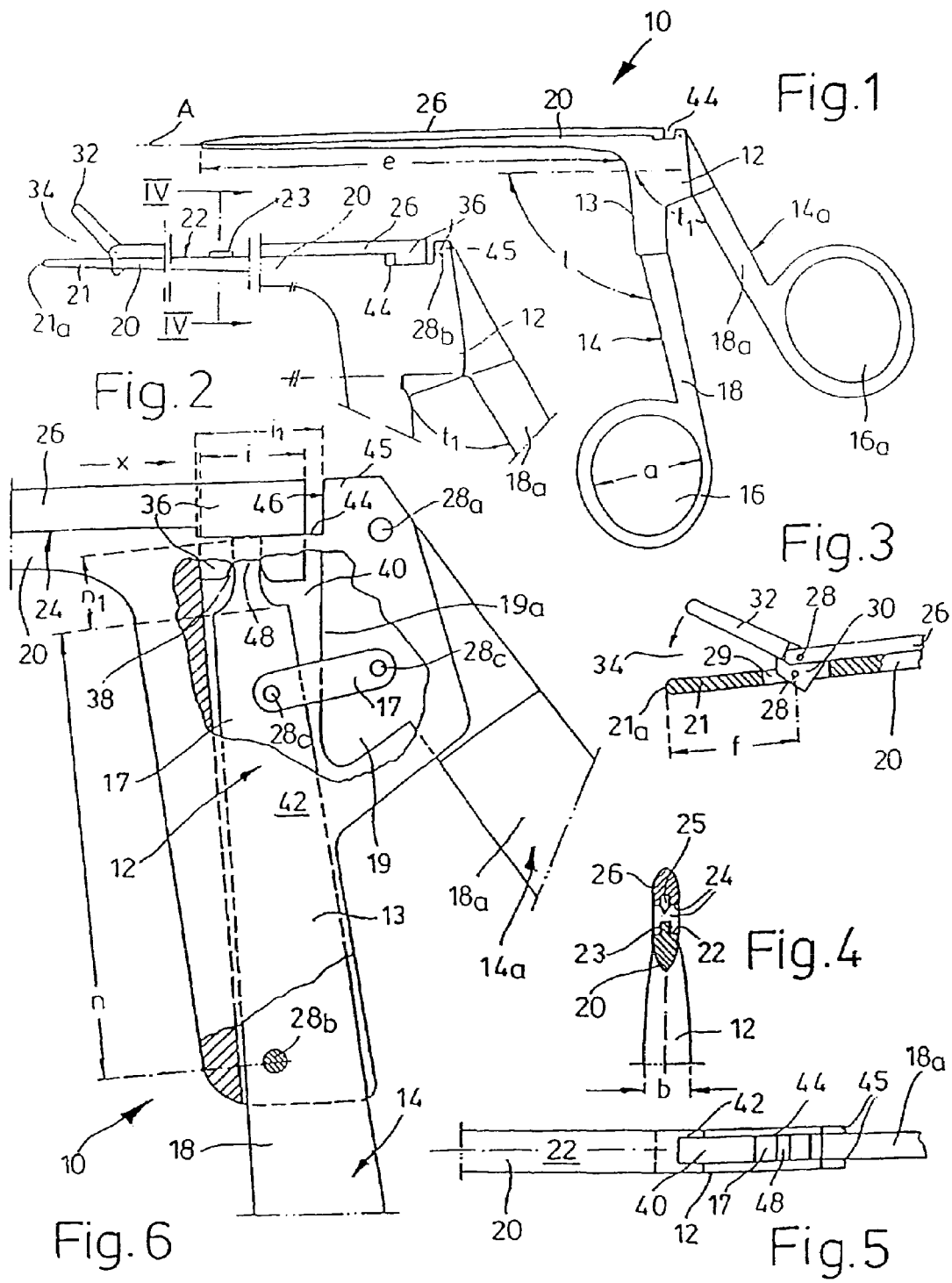

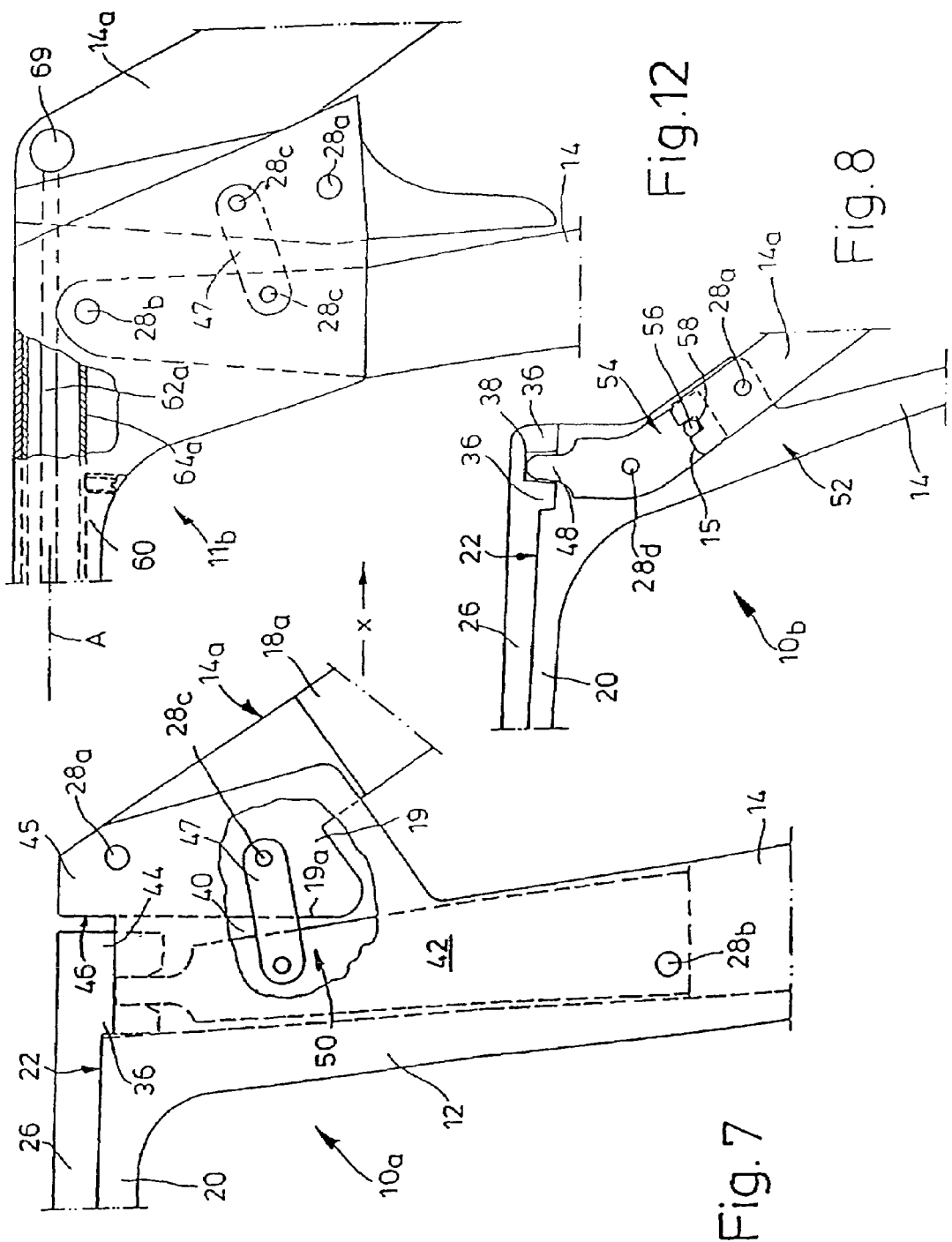

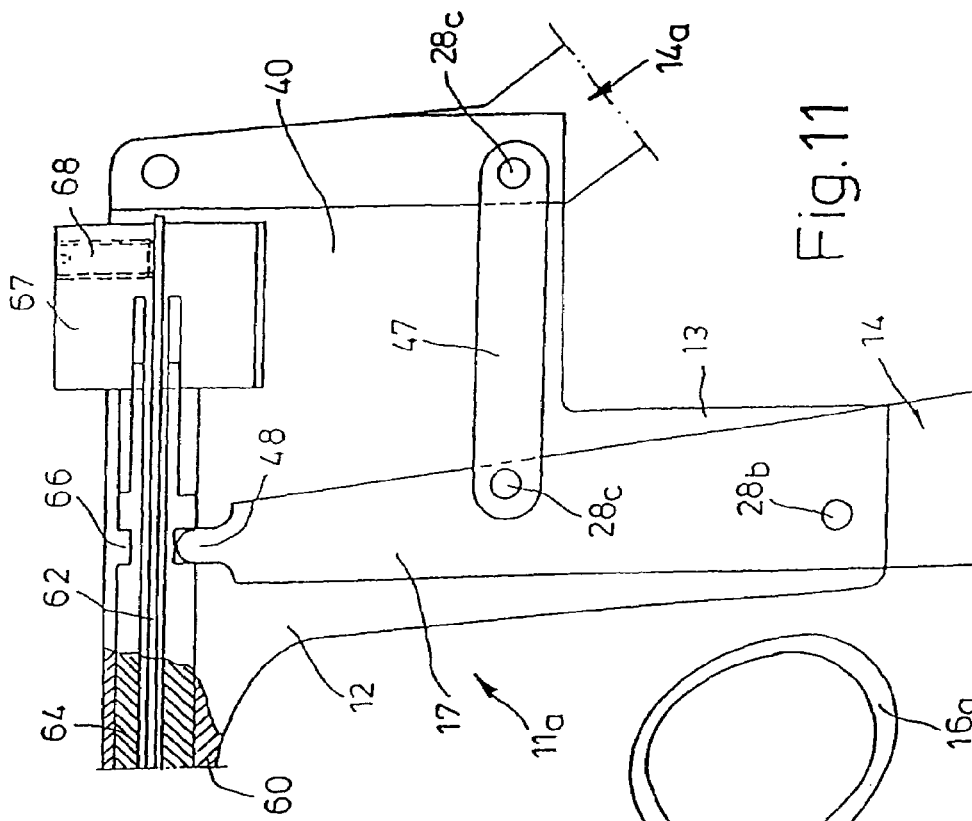
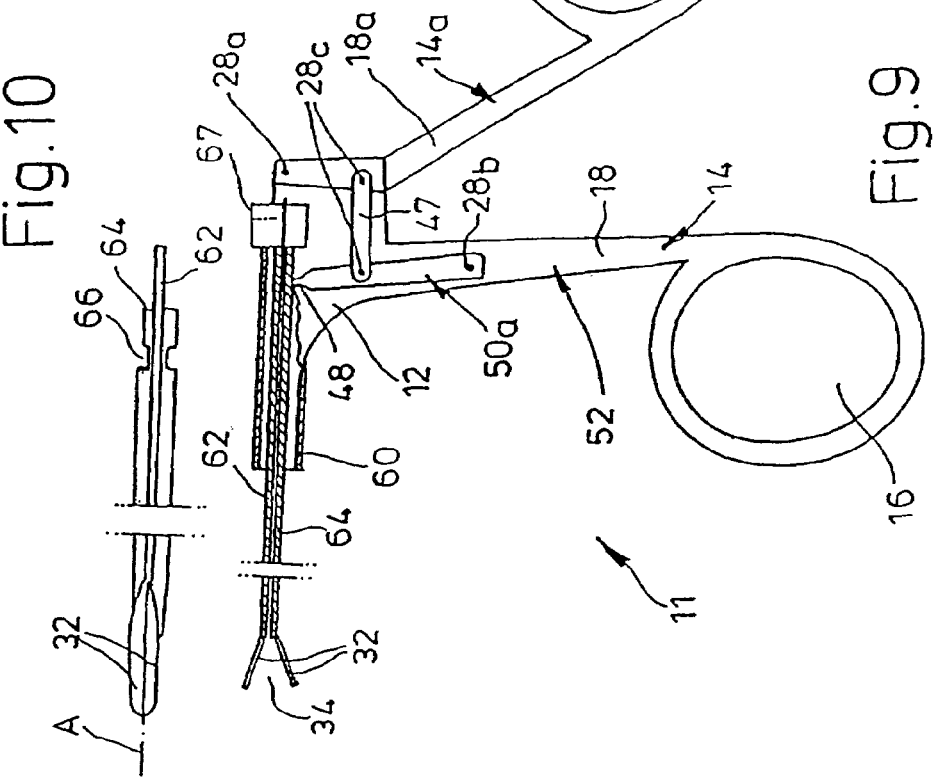

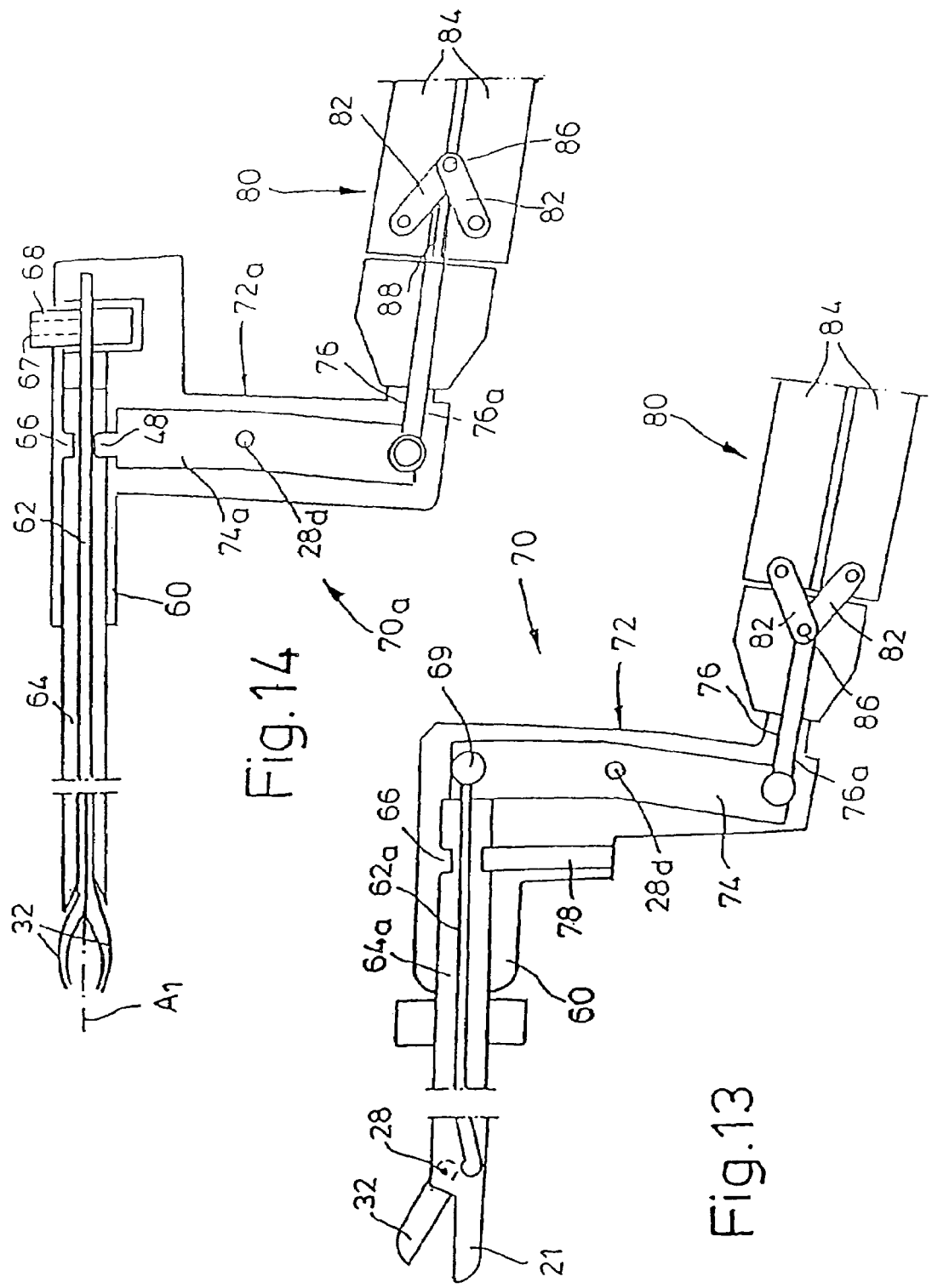

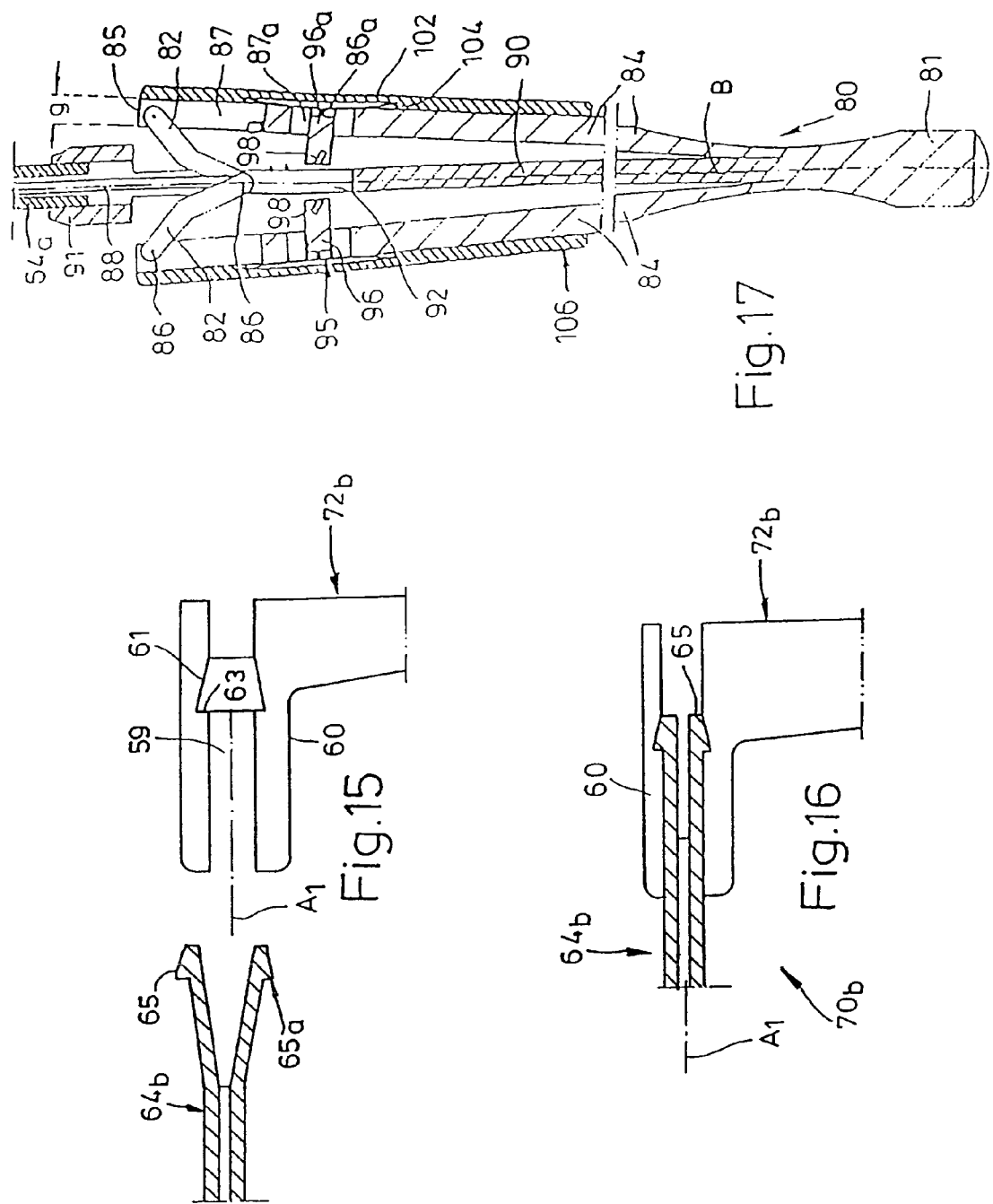

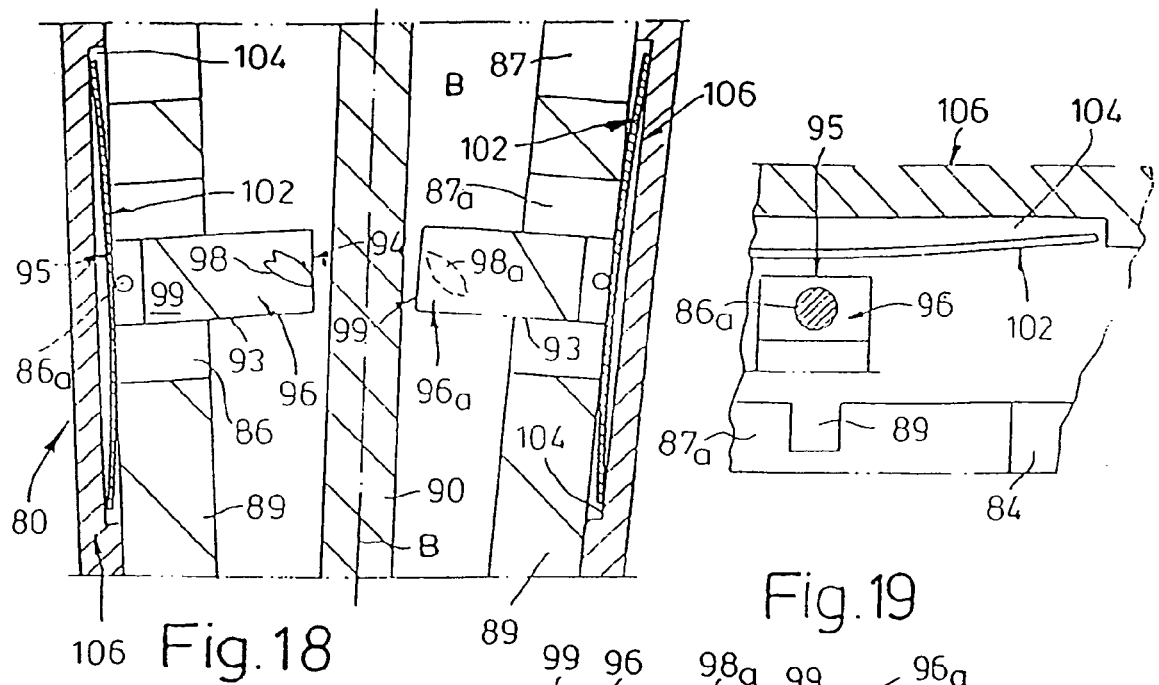
Fig. 18
Fig. 19
Fig. 21
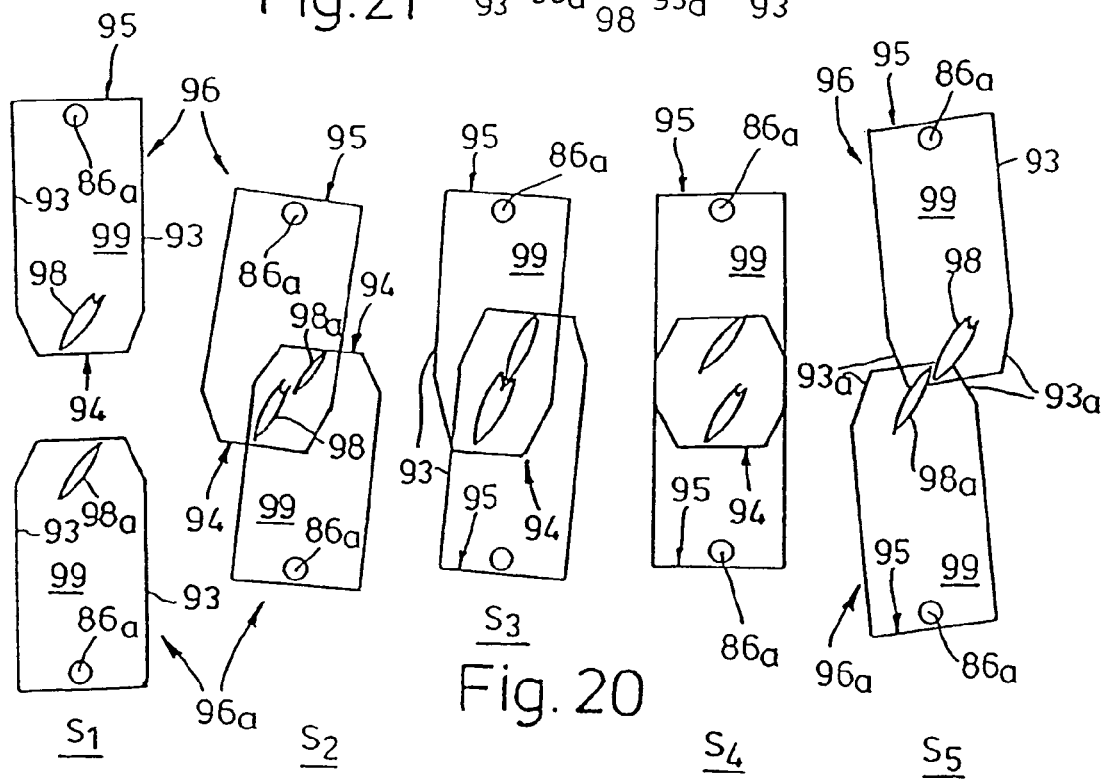
Fig. 20

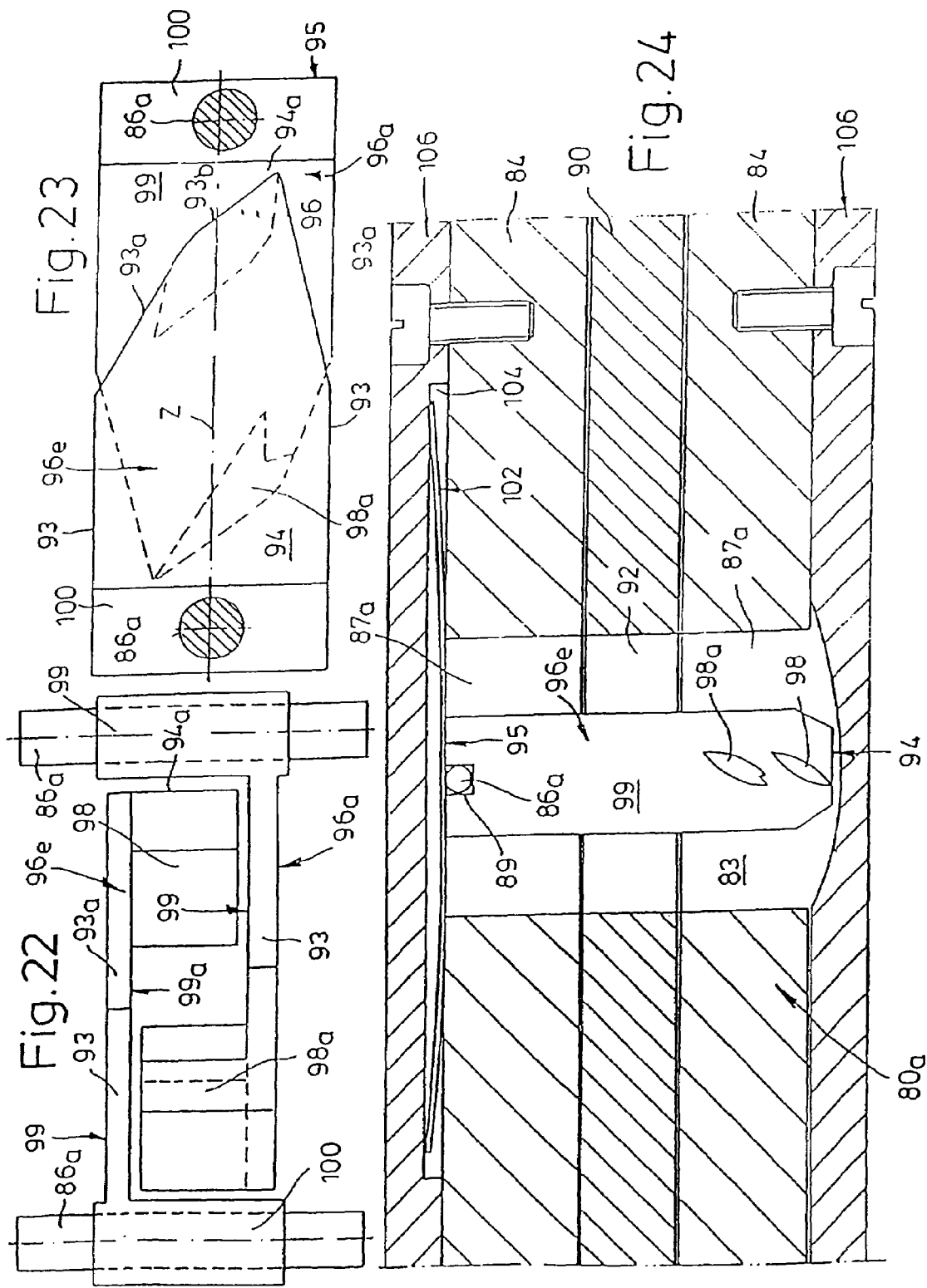

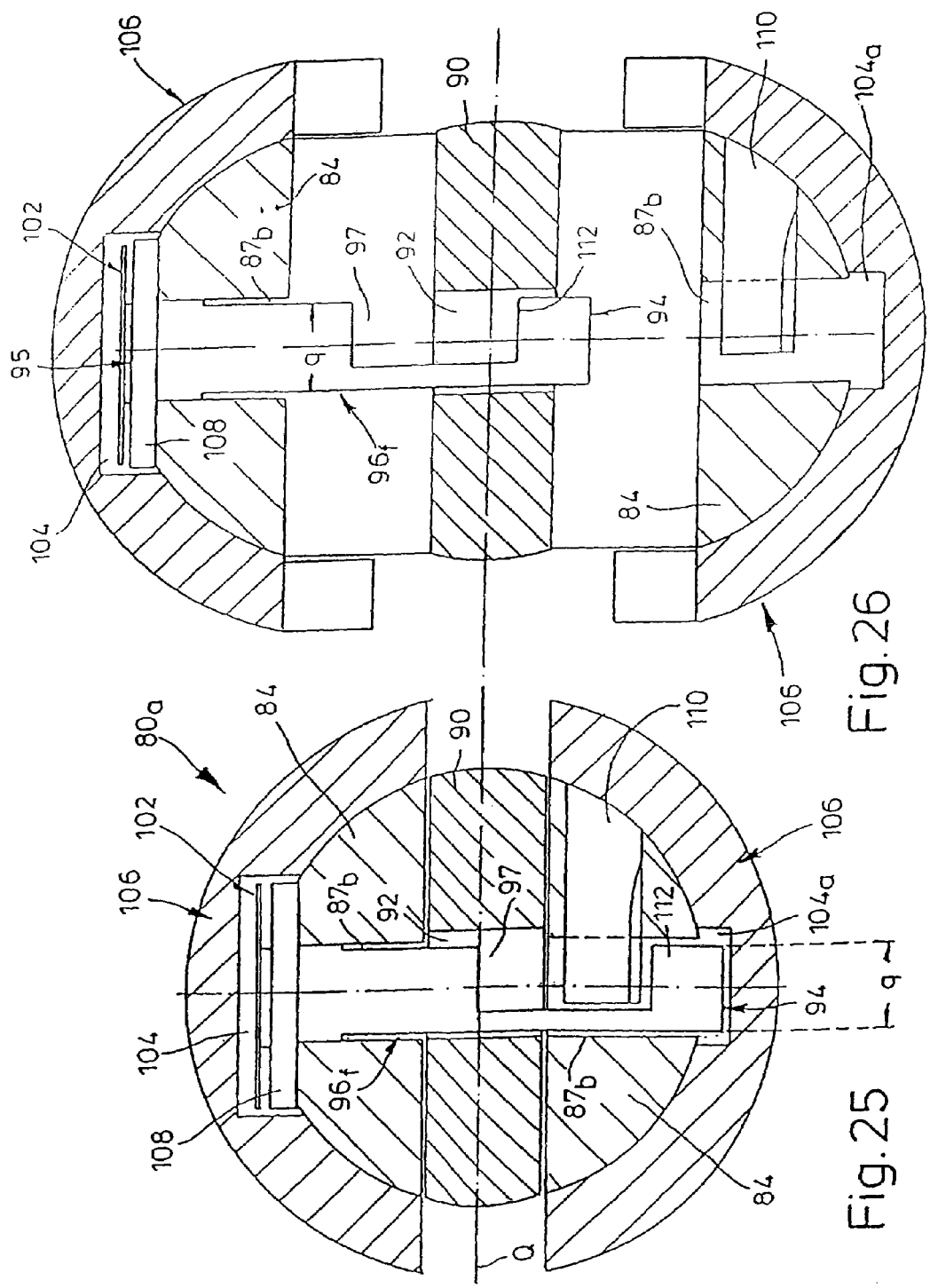

FORCEPS-LIKE SURGICAL ELEMENT

The invention relates to a forceps-like surgical element comprising lip profiles which are provided at one end, can be guided in relation to one another and delimit a clamping mouth or act in the manner of a pair of scissors, and also an actuating unit for moving at least one of the lip profiles.

DE-GM 1 836 439 by the inventor disclosed surgical forceps comprising a tubular forceps shaft and a presser and connecting rod that can be moved therein, which rod at its free end is provided with a clamping mouth consisting of a fixed lip profile and a lip profile that can be pivoted with respect thereto. A number of compression bars are articulated pivotably on each presser and connecting rod by means of hinge rods, where, when the compression bars are pressed together, the hinge rods are guided toward the mouth and in the process move one jaw of the clamping mouth and close the latter.

U.S. Pat. No. 5,906,629 describes an arthroscopy instrument comprising cutting profiles that can be guided in relation to one another. The cutting profiles are located at one end of a two-part movable shaft and can be opened and closed by a movement of the shaft elements. The shaft elements are moved via a scissor-handle-like operating element. The handle parts of the operating element are connected directly to the associated shaft elements.

German Laid-Open Specification DE 197 13 067 A1 disclosed another arthroscopy instrument which comprises a scissor-handle-like operating part, a shaft and a movable mouth part, in which the mouth part is designed as a scissors-like cutting profile. In this case, too, the handle pieces of the operating part act directly on the shaft elements.

Knowing this, the inventor set himself the aim of further developing the forceps-like surgical element mentioned above, expanding its use possibilities and above all improving the steady and reliable guidance of the instrument tip, in particular by adapting the instrument to the anatomy of the human hand and the natural movements thereof.

The teaching of the independent claim aims to achieve this object; the subclaims contain favorable developments.

According to the invention, two handle elements, which can be moved in relation to one another, are provided as an actuating unit, and each of these is joined to at least one of the lip profiles via a cord element. Forces are transmitted between at least one handle element and at least one cord element via at least one lever device that is formed separately.

In a preferred embodiment, the handle elements are scissor handles, which can pivot relative to one another and each have a holding eye, or similar implements for the fingers of a user; each of these scissor handles defines an angle with the cord element associated with it. These angles, which for example measure between 80° and 130°, in each case determine a movement range which may be the same size for both handle parts; however, it has proven to be particularly advantageous for some applications for different angular ranges to be defined.

It is within the scope of the invention to form the angle of each of the scissor handles in a variable manner for moving the lip profile(s). For this, each of the scissor handles should be articulated on a housing plate—which is the same for both of them—in which the cord elements are mounted at one end. This arrangement means that it is possible for both handle parts or scissor handles to be moved.

Instead of the two movable handle parts, in another refinement according to the invention it is also possible for just one of the scissor handles to be formed in a pivotable manner—that is to say for the angle of just one scissor handle to be variable for moving the lip profile(s). This scissor handle should also for this purpose be articulated on the abovementioned housing plate.

According to another feature of the invention, one scissor handle is articulated on the other scissor handle and the latter is fixedly connected to a cord element; a bell crank is mounted rotatably on the latter, which bell crank extends between the articulated scissor handle and the other cord element and can be connected to the latter by a rib that is integrally formed thereon and can be inserted into a countercoupling element of the other cord element. For this purpose, the bell crank may be connected to the free end of the articulated scissor handle by a catch pairing, for example by a pin or similar protrusion that projects into an opening in the other part.

According to the invention, it is also possible for both scissor handles firstly to be mounted in the housing plate in a manner such that they can pivot via in each case one hinge pin and secondly to be connected to one another via at least one hinge bracket that is articulated on both sides; said hinge pin or both scissor handles may be arranged such that they are offset in relation to one another. A rib that projects from the free end of one of the scissor handles, at a distance from its hinge pin, as a coupling element for a countercoupling element of the associated cord element has proven to be advantageous.

A further refinement according to the invention provides a scissor handle which is formed in a manner such that it can move, which scissor handle is connected, via at least one hinge bracket that is articulated on both sides, to a pivoting body that is articulated on the housing plate; in addition, in this case too a rib projects from the free end of the pivoting body as a coupling element for a countercoupling element of the associated cord element. The abovementioned hinge brackets are preferably connected to each scissor handle by a hinge pin.

The cord elements may according to the invention be two rod-like shafts, one of which is connected fixedly to the housing plate and the other of which bears on a bearing surface of the fixed shaft in a manner such that it can move axially; at least one of the two shafts should be provided with an articulated lip profile and it should be possible for the latter to pivot by the relative movement between the cords.

For the sake of better guidance of the two shafts, at least one guide web should project from the bearing surface of one shaft, which guide web projects into an axial guide slot in the bearing surface of the other shaft and is pushed into the latter when there is axial relative movement of the two shafts.

It has proven to be advantageous to articulate the pivotable lip profile at the free end of the movably mounted shaft, which lip profile can rotate about a fixed point of rotation of the other shaft relative to a lip profile arranged on the latter. A hinge plate is preferably integrally formed on the rear end of the pivotable lip profile, which hinge plate passes through the two shafts—in the region of slots—and is connected to the latter by in each case one hinge pin or similar connection. The movably mounted shaft is also provided at its rear end with a keel-like shaping which is radial to the longitudinal axis, and said shaping comprises an insertion slot as countercoupling element for the handle-side coupling element.

In another refinement according to the invention, the cord elements are formed from a tube and a tension cord that runs therein and can move relative to the tube; in this case, too, at least one of the two coaxial cord elements is provided with the articulated lip profile, and the latter is pivoted by said relative movement between the cord elements. The tube and the tension cord may according to the invention be arranged at one end in a housing, where the axially movable part is connected to a lever bracket or similar pivoting element of the housing.

Said lever bracket should be articulated on the housing approximately in the middle by a hinge pin and be connected with its one free end to the axially movable part. In one particular form—which is suitable for all refinements of the forceps-like element—the cord element is releasably connected to an associated housing by the pairing comprising a stop surface and at least one hook profile or similar counter-element which engages behind it. For this purpose, the cord element at the end has at least one hook profile which in the installation position engages behind a stop surface of the housing. In addition, the cord element at the end should have sections that can be spread relative to one another, which for their part end in each case one hook profile; the latter has, at a distance from the free end of the cord element, a profile back as counterstop for said stop surface.

In order to be able to receive and retain said hook profiles, an insertion channel or similar axial recess of the housing—provided to receive the cord element—is surrounded by an extension which forms an approximately ring-like stop surface as a grading to the insertion channel. This extension should taper longitudinally in a conical manner away from the stop surface.

Within the context of the invention, a handle having a tension element may be attached to the housing, and the tension elements may be connected to the end of the lever bracket that is remote from the axially movable parts. In addition, it is conceivable for the tube to bear in an axially movable manner and to have a radial recess or annular groove as countercoupling element for said handle-side coupling element. Or else the tension cord runs in the tube in an axially movable manner and is connected at one end to the pivotable handle element.

Overall, the result is a sliding shaft instrument in an impressively favorable refinement, which can either be moved in singly or—in stages—in a dual manner.

Further advantages, features and details of the invention emerge from the following description of preferred examples of embodiment and with reference to the drawing, in which:

FIG. 1 shows a side view of surgical forceps in the form of a sliding shaft instrument having two sliding shafts that are associated with one another;

FIG. 2 shows an enlarged detail from FIG. 1 in an operating position that has been changed with respect thereto;

FIG. 3 shows the enlarged free end region of the sliding shafts;

FIG. 4 shows the enlarged cross section through FIG. 2 on the line IV-IV with an operating position of the sliding shafts that has been changed with respect thereto;

FIG. 5 shows the plan view of a detail of the sliding shaft instrument shown in FIGS. 1, 2;

FIG. 6 to FIG. 8 show details of sliding shaft instruments in side views that have been enlarged with respect to FIG. 1;

FIG. 9 shows a side view of a tubular shaft instrument with a tension cord that is surrounded by a displaceable sheathing tube;

FIG. 10 shows the plan view of part of FIG. 9;

FIGS. 11, 12 show in each case an enlarged detail of further tubular shaft instruments;

FIGS. 13, 14 show side views of further surgical forceps on an axial handle;

FIGS. 15, 16 show a different refinement of a connection region between a shaft element and a housing of a tubular shaft instrument in two schematic sectioned side views;

FIG. 17 shows a longitudinal section through a refinement of the axial handle piece;

FIG. 18 shows an enlarged detail from FIG. 17;

FIG. 19 shows parts of FIGS. 17, 18 in an arrangement that is different with respect thereto (exploded view);

FIG. 20 shows a diagram of the manner of operation of two pendulous blocking elements of the handle in five engagement stages;

FIG. 21 shows a pair of pendulous blocking elements in the fourth of the engagement stages shown in FIG. 20, in a side view;

FIG. 22 shows an enlarged depiction of the dual pendulous blocking device shown in FIG. 21;

FIG. 23 shows the plan view of FIG. 22;

FIG. 24 shows a diagram of a pendulous blocking device shown here as a single device, which corresponds approximately to one side of the diagram shown in FIG. 18;

FIGS. 25, 26 show a cross section through another refinement of the axial handle in a closed state and in an open state.

Surgical forceps 10 as shown in FIG. 1 have two scissor handles 14, 14$_a$ which emerge from a common housing plate 12, can be moved in relation to one another and have holding eyes 16, 16$_a$ for the fingers of a user. These holding eyes 16, 16$_a$ have a width a of 20 mm, for example, and are formed out of the outer side of handle bars 18, 18$_a$ of the scissor handles 14, 14$_a$.

The left-hand scissor handle 14 in FIG. 1 is attached by its handle bar 18 to an arm strip 13—in this case having a width b of 2 mm—of the housing plate 12, said arm strip continuing the handle bar, from which housing plate there emerges, at an approximately right angle, a shaft 20 that is integral therewith and has a free length e of approximately 70 mm. The angle t between the surface 22 of the shaft 20—which surface defines a longitudinal axis A—and the front edge of the front handle bar 18 in FIG. 1 measures approximately 105°, and the angle $t_1$ between the lower surface 24 of an upper shaft 26 and the rear scissor handle 14$_a$ measures somewhat more than 120°.

As shown in FIG. 4, the shaft 20 in cross section has the approximate shape of half an ellipsis and comprises said surface that is directed upward as a bearing surface 22 for the countersurface 24 of the cross section corresponding to the upper shaft 26; both cross sections taper toward the free ends of the shafts 20, 26. From the bearing surface 22 of the lower shaft 20 there projects a comb-like short guide web 23 which engages in a longitudinal slot 25 of the upper shaft 26, said longitudinal slot guiding said web.

At a distance f of approximately 5 mm from the free edge 21$_a$ of an end piece 21 of the lower shaft 20, there is arranged in the latter a hinge pin 28, specifically in a longitudinal slot 29 of the shaft 20. Said hinge pin 28 passes through a rotatable hinge plate 30 which is pushed into the longitudinal slot 29 and is delimited therein, which hinge plate is connected by means of a second hinge pin 28 to the upper shaft 26, which ends in the region of the hinge plate 28 and has an end longitudinal slot (which cannot be seen here) for receiving the hinge plate 30. The hinge plate 30 is part of a pivoting profile 32—corresponding to the profile of the upper shaft 26—which with said end piece 21 of the lower shaft 20 forms a lip profile for a clamping mouth 34 that is defined by this pair of lip profiles. A refinement in which two scissor cutters or the like are provided instead of the clamping mouth 34 is not shown.

If the upper shaft 26 is connected in an articulated manner at its free end—as described—to the lower shaft 20, then it is provided at its other end with a keel-like shaping 36 having an axial length i of approximately 3 mm, which comprises an upwardly pointing insertion slot 38 as coupling element.

The flat radial shaping 36 is of a smaller width than its shaft 26 and points into the interior 40 the housing plate 12 that is U-shaped in plan view as shown in FIG. 5, the parallel side walls 42 of which housing plate laterally delimit said housing interior 40. Two shoulder-like edge moldings 44 that are aligned in the transverse direction and have an axial length $i_1$ of approximately 5 mm on the upper edges of the side walls 42 are in each case delimited to the rear by a crenellate cantilever web 45 the upper edge of which in FIGS. 1, 2, 6 is approximately in alignment with the outer surface of the upper shaft 26; between these cantilever webs 45, there is articulated the handle bar $18_a$ that is retained by a hinge pin $28_a$ and in FIG. 6 projects into the housing interior 40 by a nose 19. The crest $19_a$ of its nose defines a push space—as part of the housing interior 40—for receiving the other handle bar 18; the latter is articulated by means of a hinge pin $28_b$ in the groove-like arm strip 13 of the housing plate 12 and is connected to the nose 19 of the rear handle bar $18_a$ via hinge pins $28_c$ through at least one hinge bracket 47.

The push-in end 17 of the handle bar 18 tapers toward its top end, from which there projects, at a distance n from the hinge pin $28_b$, a top rib 48 having a length $n_1$ as coupling element for the shaping 36 of the upper shaft 26; the top rib 48 engages in the insertion slot 38 of the shaping 36 and can thus be moved during axial displacement of the shaft 26 about its hinge pin $28_b$.

If the upper shaft 26 is guided in the same direction by actuating the rear scissor handle $14_a$ in the pushing direction x, the shaping 36 moves toward the rear cantilever webs 45 of the housing plate 12 approximately until it comes to bear on the stop surfaces 46 of the cantilever webs 45. The clamping mouth 34 opens in the process. The movements for opening and closing the clamping mouth 34 are controlled by the thumb and index finger of the user, where the thumb is inserted in the holding eye $16_a$ of the rear scissor handle $14_a$.

This instrument 10 can be moved in a dual manner, namely to a relatively great extent by the thumb in said rear scissor handle $14_a$ and also additionally a little by the index finger placed on the other scissor handle 14.

By contrast with the above-described instrument 10, the instrument $10_a$ in FIG. 7 can only be moved in a single manner, specifically by means of the rear scissor handle $14_a$; the front scissor handle 14 is part of the fixed part of the instrument comprising housing plate 12 and lower shaft 20. In the housing interior 40, a pivoting body 50 is mounted pivotably by means of the hinge pin $28_b$, the shape of which pivoting body corresponds approximately to that of the push-in end 17 in FIG. 6. By virtue of the hinge bracket(s) 47, the movement of the scissor handle $14_a$ is transferred to said pivoting body 50.

The instrument $10_b$ of FIG. 8 can also only be moved by means of the thumb; on a fixed part 52 comprising lower shaft 20 and front scissor handle 14 made in one piece therewith, there is attached, by means of a hinge pin $28_d$, an angled bell crank 54 for changing the direction of the movable shaft 26. An edge recess 58 for a connecting pin 56 of the bell crank 54 is provided in the ridge edge 15 of the scissor handle $14_a$.

FIGS. 9, 10 show a tubular shaft instrument 11 that can be moved only singly and comprises a fixed part 52 consisting of the front scissor handle 14, the housing plate 12 and a hollow shaft 60 that projects from the latter; in said hollow shaft there is mounted, around a fixed tension cord 62, an axially movable and rotatable tubular shaft as sheathing tube 64 for controlling the articulated pivoting profile 32 of a clamping mouth 34. The sheathing tube 64 is moved by means of a pivoting body $50_a$ that is articulated on the housing plate 12, which pivoting body is connected to the pivotably mounted scissor handle $14_a$ via at least one hinge bracket 47. An end rib 48—corresponding to said top rib—of the pivoting body $50_a$ engages in a radial recess 66, for example an annular groove, of the movable sheathing tube 64, so that it is possible for axial displacement in the longitudinal axis $A_1$ to be carried out.

FIG. 11 likewise shows a movable tubular shaft as rotatable sheathing tube 64 with tension cord 62 running therein, which tension cord is held in a clamping manner at the end in an adjustment wheel 67 by a compression screw 68. The position of the clamping mouth parts 21, 32 relative to the handle can be set using the adjustment wheel 67. In this unit of a tubular shaft instrument $11_a$, which can likewise be moved in a dual manner, the push-in end 17 of the front scissor handle 14 engages in the housing plate 12, the top rib 48 of which front scissor handle is seated in its radial recess 66.

The design of an instrument $11_b$ as shown in the diagram of FIG. 12 comprises in the tubular shaft as guide tube $64_a$, which is in this case fixed, a movable tension cord $62_a$ which is connected to the rear scissor handle $14_a$ by a rotatable spherical hinge element 69. In this case—as in the example described in the introduction—the two scissor profiles 14, $14_a$ are connected by the hinge bracket(s) 46 and can be pivoted to varying extent by virtue of their mounting on hinge pins $28_b$ and $28_a$. The above-mentioned adjustment wheel 67 is also present in the example shown in this figure, but for reasons of clarity has not been shown in the drawing.

The forceps or instruments 70, $70_a$ shown in FIGS. 13, 14 that can be rotated by the adjustment wheel 67 are provided with a handle 80, as shown by way of example in FIG. 17 or—in a different form—as described in DE-GM 1 836 439. The abovementioned hollow shaft 60 is part of a housing 72, $72_a$ having an approximately "L"- or "T"-shaped contour, in which there runs a lever bracket 74, $74_a$ which is mounted at the center. The latter is connected by its lower end to handle-side tension elements 76, $76_n$.

In the refinement shown in FIG. 13, there is a fixed guide tube $64_a$ with movable tension cord $62_a$, which is attached by means of the spherical hinge element 69 to the upper end of the lever bracket 74. In this case, latching elements 78 engage in the abovementioned radial recess(es) of the guide tube $64_a$.

In the forceps $70_a$ shown in FIG. 14, the tubular shaft or the sheathing tube 64 is pushed onto the fixed tension cord 62, which in this case too is held in a clamping manner at the end by the adjustment wheel 67.

In the embodiments shown in FIGS. 13, 14, it is possible for the hand of the user of the instrument 70, $70_a$—in the viewing direction of this user which runs parallel to the tube axis or longitudinal axis $A_1$—to be taken out of the field of view; the tube axis $A_1$ is radially offset with respect to the longitudinal axis B of the handle 80. This offsetting can be designed to be parallel or at an angle, by virtue of which the instrument tip is again in alignment with the handle axis B; the double pendulous axial handle 80—which in the example shown has an integrated lock—can then be rotated between index finger and thumb in order to vary the relative association of the mouth parts 21, 32 without changing the position thereof per se.

One particular refinement of the rotatable connection of the shaft $64_b$ to the housing $72_b$ can be seen in FIGS. 15, 16; the channel 59 of the hollow shaft 60 of the housing $72_b$ is provided approximately at the transition of the housing $72_b$ into the hollow shaft 60 with a funnel molding 61 that is arranged symmetrically to the longitudinal axis $A_1$ of the tube, which funnel molding surrounds a circular stop surface 63 in the direction of the shaft $64_b$.

When said shaft $64_b$ shown in FIG. 16, which is provided at the end with hook profiles 65, is pushed into the hollow shaft 60, the hook profiles 65 engage behind the stop surface 63; the latter then bears in a retaining manner against the profile back $65_a$ of the hook profile 65.

This snap connection 61/65 between housing $72_b$ and shaft $74_b$ means that the above-described latching element 78 is not necessary.

The axial handle 80 shown in FIG. 17 has an axial central cord 90 between two handle legs 84 that start from a boss 81 and at the other end are connected by a transverse yoke consisting of two yoke brackets 82 and are designed to be resilient, on which axial central cord there is integrally formed at the end—outside the end edges 85 of the handle leg 84—a top sleeve 91. Each of the yoke brackets 82 of the transverse yoke is on one side articulated by means of a hinge pin 86 in a recess 87 of the handle leg 84 that is made in the latter over the entire width g of the handle leg 84, and both yoke brackets 82 are on the other side connected—in an axial slot 92 of the central cord 90—by means of a further hinge pin 86 to a bar 88 that passes through the top sleeve 91, which bar assumes the function of the upper shaft described in FIGS. 1 to 3, that is to say moves a lip profile 32 that is articulated at the end; the bar 88 runs in a sheathing tube $64_a$ which is seated at one end in the top sleeve 91, and this sheathing tube $64_a$ at the other end bears a fixed lip profile 21 which forms a clamping mouth 34 with the lip profile 32 of the bar 88. When the two handle legs 84 are pressed together in the direction of the axis, said bar 88 is pulled toward the boss and the clamping mouth 34 shown in FIG. 2 is closed. Another opening $87_a$ in the handle leg 84 passes through a virtually radial strip-like or pin-like blocking element 96 or $98_a$ which is fitted in the opening $87_a$ of the handle leg 84 by means of a hinge pin $86_a$. In the vicinity of the free end faces 94 of the blocking elements 96 and $96_a$, which are directed toward the central cord 90 and are delimited by parallel side edges 93—and edge sections $93_a$ that are inclined with respect thereto in FIG. 20—there is provided in each case one engagement member 98 or $98_a$ which is either molded into the blocking element 96, $96_a$ or else projects beyond the opposed surfaces 99, $99_a$ of the blocking elements 96, $96_a$. The other end face 95 that is adjacent to the hinge pin $86_a$ is associated with a leaf spring 102; the latter lies in a flat inner recess 104 of a handle shell 106 that is fitted on the outside of the handle leg 84. For this purpose, FIG. 19 shows that said hinge pin $86_a$ runs in a transverse groove 89 of the handle leg 84 that is open toward the leaf spring 102, which transverse groove for its part is arranged in the longitudinal center of said opening $87_a$.

As already mentioned, the engagement members 98, $98_a$ of the blocking elements may be either hook- and counterhook-like moldings or shapings made on the surface 94. The latter case is shown in FIGS. 20, 21, where FIG. 20 shows five different states or positions of a dual pendulous system:

$S_1$: open;
 $S_2$: during latching-in;
 $S_3$: latched;
 $S_4$: during latching-out;
 $S_5$: almost open.

The example of a dual pendulous system shown in FIGS. 22, 23 shows two clamping elements 96, $96_a$ lying above one another, each of which has a hinge web 100 molded integrally thereon at the end, which hinge web is passed through by a hinge pin $86_a$. The free edge of the blocking element 96, $96_a$ which projects in a tongue-like manner from its hinge web 100 is defined by three edge sections 93, $93_a$ that are inclined with respect to one another and form a tip $94_a$ that lies outside the longitudinal axis Z of the tongue. The engagement member $98_a$ of the lower blocking element $96_a$—like that shown in FIG. 20—in plan view has a dovetail-like end; the other engagement member 98 is shaped like a lozenge and engages in the closed position in said end of the other engagement member $98_a$.

In the single pendulous system of the axial handle $80_a$ shown in FIG. 24, the blocking element $96_e$, which in this case is formed in one piece, is associated at one end with the abovementioned leaf spring 102 and by means of its hinge pin $86_a$—as shown in the diagram in FIG. 19—is connected to the transverse groove 89 of its handle leg 84, passes through the central cord 90 and engages in the opening $87_a$ of the other handle leg 84, from the base 83 of which there projects the abovementioned engagement member $98_a$ having a dovetail-like end; the latter interacts with the other engagement member 98 fitted on the lower surface of the clamping element, in the manner described.

FIGS. 25, 26 also show a single pendulous system of an axial handle $80_a$. The inner recess 104 is provided with the leaf spring 102 for its upper handle shell in the drawing; said leaf spring presses against the associated end face 95 of the single blocking element $96_f$, which in the region of said inner recess 104 is mounted on the outer surface of the handle leg 84 by means of a transverse profile 108. Said handle leg is passed through by the strip-shaped blocking element $96_f$ in the region of a radial opening $87_b$ that is strip-shaped in plan view, which blocking element passes through the axial slot 92 of the central cord 90 and is pushed through the radial opening $87_b$ of the other handle leg 84 when the two handle halves are brought together; its free end face 94 then projects, as shown in FIG. 25, into an inner recess $104_a$ of the other handle shell 106, this inner recess corresponding to the width q of the clamping element 96 with play.

In the closed position, a twistlock 110 that is parallel to the transverse axis Q of the axial handle $80_a$ engages in a lateral molding 97 of the clamping element $96_f$ as a stop for the top section 112 of the individual clamping element $96_f$. The twistlock 110 is either part of the handle leg 84 or part of the handle shell 106.

The invention claimed is:

1. Forceps-like surgical element, comprising lip profiles (21, 32) that are provided at one end and guided in relation to one another and delimit a clamping jaw (34), an actuating unit for moving at least one of the lip profiles (21, 32), the actuating unit being provided in the form of two grip arms (84) that can be moved relative to one another, wherein the grip arms (84) are connected via a tension cord (88) to at least one of the lip profiles (21, 32), wherein the tension cord (88) extends within a tube (64) and is movable relative to the tube, one of the lip profiles (21, 32) being able to be pivoted through the relative movement between the tension cord (88) and the tube (64), the tension cord (88) being mounted in the tube (64) so as to be axially movable therein and being attached to an axial grip (80) that can be acted on by radial pressure and comprises the grip arms (84), and wherein a blocking element (96, 96a) is provided, which is fitted by a hinge pin (86a) in a hole (87a) in one of the grip arms (84), characterized in that the front face (95) of the blocking element (96, 96a) adjacent to the hinge pin (86a) is assigned a leaf spring (102), and wherein said leaf spring (102) presses against said front face (95).

2. Element according to claim 1, characterized in that the blocking element (96, 96a) extends at least approximately perpendicular to the leaf spring (102).

3. Element according to claim 1, characterized in that the blocking element (96, 96a) is designed as an almost radial strip or stud.

4. Element according to claim 1, characterized in that an engagement member (98, 98c) is provided near a free front end (94) of the blocking element (96, 96a).

5. Element according to claim 1, characterized in that the leaf spring (102) is mounted in an inner recess (104) arranged externally on the grip arm (84).

6. Element according to claim 1, characterized in that the hinge pin (86a) extends within a transverse groove (89) of the grip arm (84), which transverse groove (89) is open toward the leaf spring (102).

7. Element according to claim 6, characterized in that the blocking element (96, 96a) engages through a central cord (90) of the axial grip (80).

8. Element according to claim 1, characterized in that two blocking elements (96, 96a) are provided, which are component parts of a dual oscillation system.

9. Element according to claim 1, characterized in that a single blocking element (96) is provided, which is a component part of a single oscillation system.

10. Element according to claim 1, characterized in that the engagement member (98a) of the single blocking element (96) articulated on one of the grip arms (84) interacts with an engagement member (98) of the other grip arm (84).

11. Element according to claim 1, characterized in that the movable tension cord (88) enclosed by the tube (64) is designed such that it can be partially drawn into the axial grip (80) by means of the radial pressure with respect to the longitudinal axis (B) of the axial grip (80).

* * * * *